(12) United States Patent
Chin (10) Patent No.: US 10,667,839 B2
(45) Date of Patent: *Jun. 2, 2020

(54) TISSUE REMOVING DEVICE (71) Applicant: Boston Scientific Scimed, Inc., Maple Grove, MN (US)

(72) Inventor: Yem Chin, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 178 days.

This patent is subject to a terminal disclaimer.

(21) Appl. No.: 15/350,907

(22) Filed: Nov. 14, 2016

(65) Prior Publication Data

US 2017/0119429 A1 May 4, 2017

Related U.S. Application Data (60) Continuation of application No. 14/570,021, filed on Dec. 15, 2014, now abandoned, which is a
(Continued)

(51) Int. Cl.
*A61B 17/3207* (2006.01)
*A61B 90/00* (2016.01)
(Continued)

(52) U.S. Cl.
CPC ......... *A61B 17/320758* (2013.01); *A61B 17/32002* (2013.01); *A61B 17/320016* (2013.01); *A61B 17/320783* (2013.01); *A61B 90/37* (2016.02); *A61B 10/0096* (2013.01); *A61B 10/0275* (2013.01); *A61B 10/0283* (2013.01); *A61B 17/320725* (2013.01); *A61B 2017/00057* (2013.01); *A61B 2017/00199* (2013.01); *A61B 2017/00274* (2013.01); *A61B 2017/00287* (2013.01); *A61B 2017/32007* (2017.08); *A61B 2017/320024* (2013.01);
(Continued)

(58) Field of Classification Search
CPC ............ A61B 17/32; A61B 17/320016; A61B 17/320024; A61B 17/320032; A61B 17/320064; A61B 17/320758; A61B 17/320775; A61B 10/04
See application file for complete search history.

(56) References Cited

U.S. PATENT DOCUMENTS 3,472,230 A 10/1969 Fogarty
4,881,550 A 11/1989 Kothe
(Continued)

FOREIGN PATENT DOCUMENTS

EP 0706781 4/1996

OTHER PUBLICATIONS

International Search Report and Written Opinion dated Apr. 7, 2008, issued in PCT/US07/22867.
(Continued)

*Primary Examiner* — Patrick Fernandes
(74) *Attorney, Agent, or Firm* — Bookoff McAndrews, PLLC (57) ABSTRACT Tissue can be removed from a patient with a catheter or other medical device having a cutting member. A source of suction can be coupled to the device for suctioning removed tissue through a lumen in the device and out of the patient's body.

19 Claims, 6 Drawing Sheets

Related U.S. Application Data continuation of application No. 13/438,164, filed on Apr. 3, 2012, now Pat. No. 8,945,021, which is a continuation of application No. 12/819,723, filed on Jun. 21, 2010, now abandoned, which is a division of application No. 11/928,987, filed on Oct. 30, 2007, now abandoned.

(60) Provisional application No. 60/856,182, filed on Nov. 1, 2006.

(51) Int. Cl.
*A61B 17/32* (2006.01)
*A61B 90/30* (2016.01)
*A61B 10/00* (2006.01)
*A61B 10/02* (2006.01)
*A61B 17/00* (2006.01)

(52) U.S. Cl.
CPC ............ *A61B 2017/320032* (2013.01); *A61B 2017/320064* (2013.01); *A61B 2017/320733* (2013.01); *A61B 2090/306* (2016.02); *A61B 2090/309* (2016.02)

(56) References Cited

U.S. PATENT DOCUMENTS

| | | | |
|---|---|---|---|
| 4,976,269 | A | 12/1990 | Mehl |
| 4,979,951 | A | 12/1990 | Simpson |
| 4,994,024 | A | 2/1991 | Falk |
| RE33,569 | E | 4/1991 | Giddord, III et al. |
| 5,195,533 | A | 3/1993 | Chin et al. |
| 5,226,909 | A | 7/1993 | Evans et al. |
| 5,250,059 | A | 10/1993 | Andreas et al. |
| 5,488,958 | A | 2/1996 | Topel et al. |
| 5,526,822 | A | 6/1996 | Burbank et al. |
| 5,562,694 | A | 10/1996 | Sauer et al. |
| 5,569,284 | A * | 10/1996 | Young ............ A61B 17/32002 604/22 |
| 5,584,796 | A | 12/1996 | Cohen |
| 5,665,062 | A | 9/1997 | Houser et al. |
| 5,674,235 | A | 10/1997 | Parisi |
| 5,715,832 | A | 2/1998 | Koblish et al. |
| 5,782,764 | A | 7/1998 | Werne |
| 5,836,953 | A | 11/1998 | Yoon |
| 5,848,978 | A | 12/1998 | Cecchi |
| 5,913,857 | A | 6/1999 | Ritchart et al. |
| 5,921,943 | A | 7/1999 | Kass et al. |
| 5,957,936 | A | 9/1999 | Yoon et al. |
| 6,039,748 | A | 3/2000 | Savage et al. |
| 6,156,049 | A | 12/2000 | Lovato et al. |
| 6,165,136 | A | 12/2000 | Nishtala |
| 6,165,166 | A | 12/2000 | Samuelson et al. |
| 6,383,194 | B1 | 5/2002 | Pothula |
| 6,428,486 | B2 | 8/2002 | Ritchart et al. |
| 6,432,111 | B1 | 8/2002 | Ternstrom |
| 6,468,228 | B1 | 10/2002 | Topel et al. |
| 6,537,273 | B1 | 3/2003 | Soslak et al. |
| 6,589,252 | B2 | 7/2003 | McGuckin, Jr. |
| 6,676,658 | B2 | 1/2004 | Burbank et al. |
| 6,758,824 | B1 | 7/2004 | Miller et al. |
| 2002/0013580 | A1 | 1/2002 | Houser et al. |
| 2002/0026127 | A1 | 2/2002 | Balbierz et al. |
| 2004/0225310 | A1 | 11/2004 | Culp et al. |
| 2004/0243157 | A1 | 12/2004 | Connor et al. |
| 2005/0070892 | A1 | 3/2005 | Ciarrocca |
| 2005/0187491 | A1 | 8/2005 | Burbank et al. |
| 2006/0030785 | A1 | 2/2006 | Field et al. |
| 2006/0047219 | A1 | 3/2006 | Baruti et al. |
| 2006/0258955 | A1 | 11/2006 | Hoffman et al. |

OTHER PUBLICATIONS

International Preliminary Report on Patentability and Written Opinion of the International Searching Authority for International Application No. PCT/US2007/022867, dated May 5, 2009 (8 pages).
"Resectr Tissue Resection Device," Resectr Product Overview—Boston Scientific, accessible at https://www.bostonscientific.com/en-EU/products/uterine-tissue-removal-systems/resectr-product-overview.html. last accessed Dec. 23, 2019, 4 pages).

* cited by examiner

TISSUE REMOVING DEVICE

This application is a continuation of U.S. patent application Ser. No. 14/570,021, filed Dec. 15, 2014, which is a continuation of U.S. patent application Ser. No. 13/438,164, filed Apr. 3, 2012, now U.S. Pat. No. 8,945,021, which is a continuation of U.S. patent application Ser. No. 12/819,723, filed Jun. 21, 2010, now abandoned, which is a divisional of U.S. patent application Ser. No. 11/928,987, filed Oct. 30, 2007, now abandoned, which claims the benefit of priority to U.S. Provisional Patent Application No. 60/856,182, filed Nov. 1, 2006, all of which are incorporated herein by reference in their entireties.

TECHNICAL FIELD

The present invention relates to removing tissue from a patient and to medical devices and procedures for removing tissue.

BACKGROUND INFORMATION

Minimally invasive surgery generally reduces patient trauma and speeds recovery time as opposed to more conventional surgical procedures in which a large portion of the patient's body is opened. Minimally invasive endoscopic surgery generally involves incising through body walls for examining, viewing, and/or operating on various bodily organs or structures, including the ovaries, uterus, gall bladder, bowels, kidneys, appendix, etc. In such endoscopic procedures, a trocar typically creates an incision and trocar tubes or cannula devices are extended into and left in place (in, for example, the abdominal wall) so that endoscopic surgical tools may be inserted into the patient's body. A camera or endoscope can be inserted to enable visual inspection and magnification of a cavity in the body of the patient. The surgeon then performs the desired procedure with the aid of specialized instrumentation designed to fit through additional openings which provide additional entries into the desired body cavity. Thus, instead of a rather large incision (typically 12 inches or larger) necessary to complete a more conventional fully invasive surgical procedure, minimally invasive endoscopic surgery results in one or several smaller incisions, usually between 5 and 15 millimeters in size. In most instances, recovery is quicker and less painful than conventional surgery. In addition, because the surgical field typically is greatly magnified, surgeons are often better able to dissect blood vessels and control blood loss. In addition, heat and water loss are often reduced as a result of the smaller incisions.

In some surgical procedures, it is necessary to remove tissue or diseased organs. This can be challenging during endoscopic surgery because the tissue or organ removal must be achieved through the small openings through which the procedure is performed. In these situations, it may be desirable to fragment, morcellate, or otherwise reduce body tissue into smaller pieces that can be readily removed through the small endoscopic openings.

Morcellation involves fragmenting and removing diseased tissue or organ parts from healthy tissue or organs. In endoscopic morcellation, the fragmented pieces are typically removed from the patient's body through a small incision or through a trocar cannula device which extends through the abdominal wall. When the tissue or organ part is diseased or infected, it is preferred that the excised portions thereof be isolated from contact with surrounding healthy tissue. Accordingly, it is often necessary to enclose the fragmented organ during removal, thus preventing contamination of healthy tissue and bodily organs. In some instances, the organ is fragmented in a bag by a surgical device known as a morcellator, until such a time as the entire specimen is small enough to be removed while in the bag from the abdominal cavity through one of the minimally invasive endoscopic openings.

SUMMARY OF THE INVENTION

The invention generally relates to removing tissue from a patient in a minimally invasive manner. The patient can be a human or other mammal, for example. A catheter or other medical device for removing tissue in accordance with the invention can be inexpensive and easy to manufacture.

In one aspect, the invention relates to a medical device for removing tissue from a patient. The medical device comprises an outer catheter including a distal end and defining a lumen and a tubular member defining a lumen and an opening for cutting tissue within the body of a patient. The lumen of the tubular member is couplable to a suction source to provide suction through the opening. The tubular member is disposed movably within the lumen of the outer catheter such that at least a portion of the tubular member is extendable beyond the distal end of the outer catheter to engage tissue within the opening. The tubular member is configured to cut the engaged tissue when the tubular member is moved with respect to the outer catheter, the cut tissue being transported through the lumen of the tubular member when the suction source is coupled to lumen of the tubular member.

Embodiments according to this aspect of the invention can include the following features. The opening can be elongate and be defined at least in part by two substantially parallel edges. At least one of the edges can define a cutting member for cutting the engaged tissue. The cutting member can be configured to cut the engaged tissue when the tubular member is rotated about a longitudinal axis of the outer catheter. Additionally or alternatively, the cutting member can be configured to cut the engaged tissue when the tubular member is moved along a longitudinal axis of the outer catheter. The medical device can further comprise an ultrasound device operably coupled to the cutting member and being adapted to facilitate cutting tissue. Moreover, the cutting member can includes an active cord cautery device, such as a monopolar or bipolar cautery device. The medical device can further include a light source configured to facilitate determining the location of the opening while inside of a patient. The light source can include a fiber optic element and/or a light emitting diode.

In another aspect, the invention involves a system comprising a medical device as described above and a computer interface coupled to the medical device and capable of providing signals representative of a visual image of an internal portion of the body of the patient. In certain embodiments, the system includes a bag coupled to the medical device for collecting a tissue sample and/or a suction source adapted and configured to provide suction through the lumen.

In another aspect, the invention involves a medical device comprising a main body portion including a distal end and a cutting member operably coupled to the distal end of the main body portion. The main body portion defines a longitudinal axis, and the cutting member is configured to rotate about an axis transverse to the longitudinal axis from a first position to a second position when performing a cutting operation.

Embodiments according to this other aspect of the invention can include the following features. The main body portion can define a lumen along at least a portion of its length, a distal port at the distal end, and a proximal port proximal to the distal end. The proximal port can be in fluid communication with a suction source for removing tissue cut by the cutting member through the distal port and the lumen. The cutting member can have a substantially arcuate shape and circumscribe a volume when moved from the first position to the second position. The medical device can further include an actuator for moving the cutting member from the first position to the second position. The actuator can include a wire having a distal end, the distal end of the wire being operably coupled to the cutting member and being configured to circumscribe an arcuate path when the wire is moved along the longitudinal axis. The main body portion can define a lumen and the wire can be disposed within the lumen. The wire can be made from spring steel and/or a shape memory material, such as a nickel-titanium alloy. The cutting member can be caused to move from the first position to the second position when the wire is advanced in a proximal or distal direction with respect to the main body portion. The actuator can alternatively move the cutting member from the first position to the second position by applying an electromagnetic force thereto. The actuator and the cutting member can accordingly be configured to carry electrical currents in opposing paths. The medical device can further include a switching mechanism, a power supply and a controller operably associated with the switching mechanism and power supply, the controller adapted to operate the switching mechanism to alternate electrical current flowing through the actuator and cutting member to cause the cutting member to oscillate between the first position and the second position.

In yet another aspect, the invention features a medical device comprising a main body portion defining a lumen therethrough and including a distal end, and a shaft rotatably disposed in the lumen of the main body portion. The shaft includes a proximal end and a distal end, and the shaft is capable of rotation with respect to the main body portion about a longitudinal axis. The device further comprises a rotational drive source operably coupled to the proximal end of the shaft and a substantially arcuate cutting member, whereby a proximalmost end of the substantially arcuate cutting member is attached to the distal end of the shaft. The cutting member is configured to circumscribe a volume about the longitudinal axis when the shaft is rotated. A compartment is affixed to the distal end of the main body portion, and the compartment is configured to house the cutting member.

Embodiments according to this aspect of the invention can include the following features. The main body portion can define a second lumen therethrough, the second lumen having a distal port proximate the cutting member and a proximal opening proximal to the distal end of the main body portion. A suction source can be coupled to the compartment by way of the second lumen to facilitate removal of tissue from a patient.

In still another aspect, the invention relates to a medical device comprising a main body portion including a distal end and defining a lumen therethrough. The medical device also comprises a rotatable cutting member disposed in the lumen. The cutting member is defined by at least one helical cutting edge and defines at least one helical channel therethrough, and the cutting member is capable of being disposed beyond the distal end of the main body portion.

Embodiments according to this aspect of the invention can include the following features. The cutting member can be moved in a rotational and/or longitudinal direction with respect to the main body portion. A suction source can be coupled to the medical device to facilitate removal of tissue from a patient through the lumen.

In a further aspect, the invention features a medical device comprising a main body portion including a distal end and defining a lumen therethrough. The device also comprises a shaft slidably disposed through the lumen of the main body portion. The shaft includes a distal end and a cup shaped cutting member attached to the distal end of the shaft. The cutting member includes a cutting edge disposed proximate to a rim of the cup shaped cutting member, and the cutting member is configured to cut tissue when advanced in a proximal direction with respect to the main body portion of the medical device.

Embodiments according to this aspect of the invention can include the following features. The cutting member can protrude from the distal end of the main body portion. The main body portion can include a closed end that defines a tissue entry port through a sidewall of the main body portion suitable to permit entry of tissue to be removed from a patient.

In still a further aspect, the invention features a method of removing tissue from a patient. The method comprises providing a medical device including a main body portion and a cutting member slidably coupled thereto, introducing the medical device through the urethra of a patient, removing tissue from the patient by advancing the cutting member in a proximal direction with respect to the main body portion, and withdrawing the medical device from the patient. Tissue can be removed from, for example, the patient's bladder or the prostate gland.

Both the foregoing and following descriptions are exemplary and illustrative. The accompanying drawings, which are incorporated in and constitute part of this specification, are included to illustrate and provide a further understanding of the invention and particular embodiments thereof. The drawings are not necessarily to scale and generally serve to help illustrate the principles and/or certain embodiments of the invention.

DESCRIPTION

The devices and methods presented, described, and shown herein may be used for resecting tissue from within the body of a patient and removing the resected tissue from the patient's body, for example. Medical devices and procedures according to the invention are particularly well suited for resecting cancerous growths from the bladder and/or the prostate gland of a patient.

Figure 1A:
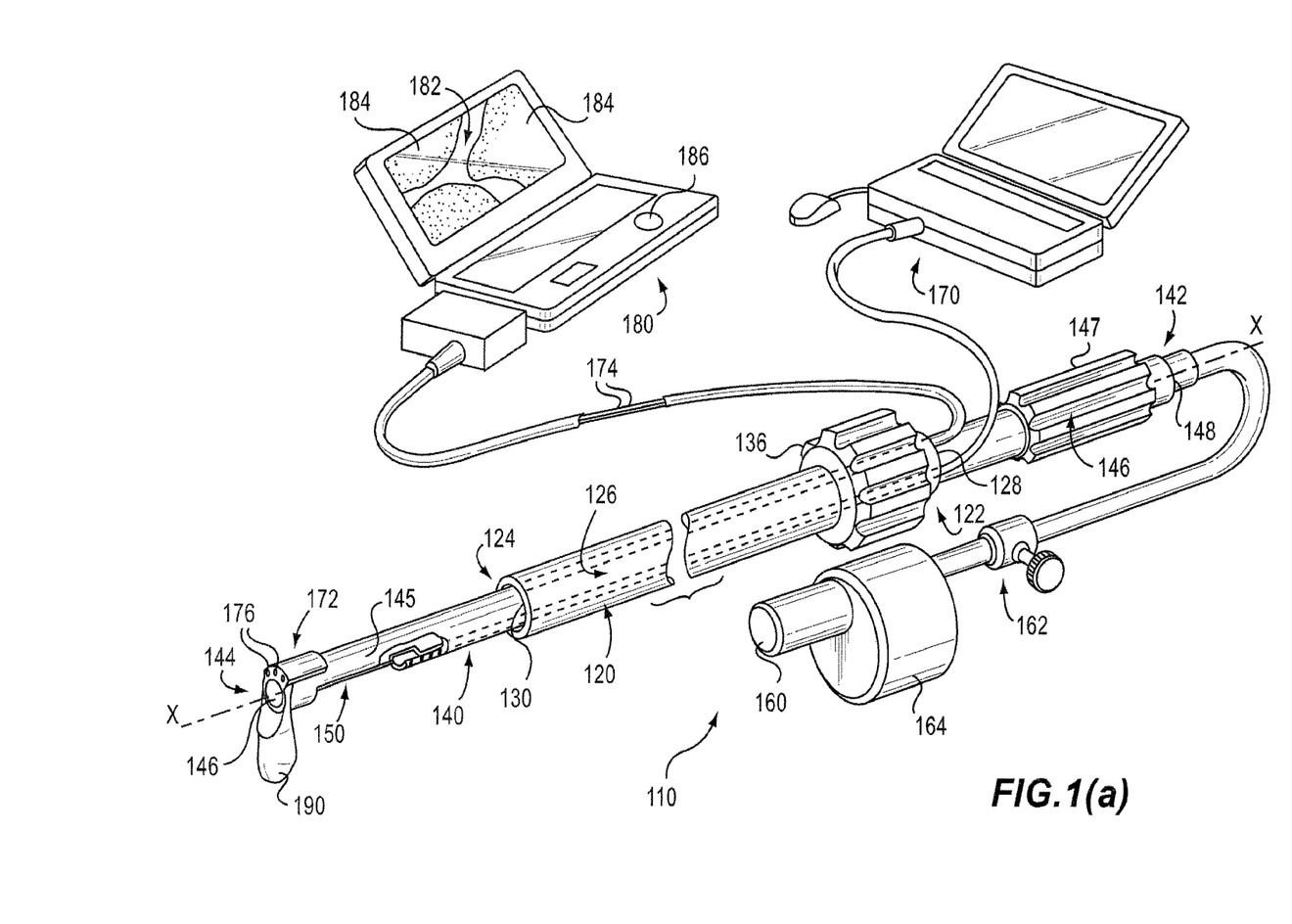
FIG. 1(a) is a schematic representation of a first representative embodiment of a medical device made in accordance with the present invention.

For purpose of explanation and illustration, and not limitation, a partial view of an exemplary embodiment of the medical device in accordance with the invention is shown in FIG. 1(a) and is designated generally by reference character 110. Other embodiments of a system in accordance with the invention, or aspects thereof, are provided in FIGS. 2-5, as will be described.

In accordance with one aspect of the invention, an outer catheter of a medical device includes a distal end and defines a lumen.

For purposes of illustration and not limitation, as embodied herein and as depicted in FIG. 1(a), a medical device 110 has an outer catheter 120 which includes a proximal end 122, a distal end 124, and defines a lumen 126 therethrough. Lumen 126 includes a proximal port 128 and a distal port 130. Outer catheter 120 can be further coupled to a handle 136 proximate its proximal end 122 for gripping by an operator such as a surgeon or other medical professional. The handle can be attached to outer catheter 120 by, for example, welding, use of an adhesive, or forming the handle integrally with outer catheter 120. Other ways of attachment also are possible.

Outer catheter 120 can be made from any one of a variety of materials including metal, plastic, and composite materials. Combinations of such materials also can be used to form the outer catheter. For example, the outer catheter 120 can be made of a fiber reinforced plastic. The outer catheter 120 can also be constructed of a braided reinforcement layer over a lubricious inner layer such as tetrafluoroethylene (Teflon or TFE). The braid can be oversleeved or overextruded or coextruded with a thermoplastic polymer such as Nylon or Pebax graded to provide the appropriate rigidity. The braid material can be Liquid Crystal Polymer, sold as Vectran, in mono or multifilament. The braid material can also include metallic wire in one or more carriers. These wires can be stainless steel or a more radiopaque metal such as platinum. The polymer oversleeve can also be filled with a material such as barium to enhance radiopacity. A hydrophilic coating can be added to the outer catheter to improve lubricity. A knitted configuration or a coil can also substitute for the braid.

Other examples of materials from which the outer catheter 120 can be formed include silicone, nylons, urethanes and thermoplastic materials such as TFE, high density polyethylene (HDPE), law density polyethylene (LDPE), polypropylene (PP), polyethylene (PE), and PEEK™ polymer. In general, any material or combination of materials used to make the outer catheter 120 should result in the outer catheter 120 being biocompatible, because at least a portion of the outer catheter 120 typically will be inserted into the body of a mammal (such as a human patient) when the medical device 110 is used for its intended purpose. Outer catheter 120 can have a uniform stiffness along its length, or a stiffness that increases or decreases along its distal length, as desired for the particular application. Adjusting the stiffness can be accomplished by varying the thickness of outer catheter 120, or by adjusting the properties and/or composition of the outer catheter. For example, a braided layer can be impregnated along a polymeric outer catheter 120 along a part of its length, providing an outer catheter 120 with a stiff proximal segment and a flexible distal segment. If polymers are used, it is possible to adjust the blend of polymers or method of curing the polymer along the length of catheter 120 to achieve a desired stiffness profile. Other ways of adjusting the stiffness and/or making the outer catheter more or less flexible or inflexible also can be employed.

As indicated in FIG. 1(a), the medical device 110 further includes a tubular member 140 including a proximal end 142, a distal end 144, and a sidewall 145, and the tubular member 140 also defines a lumen 146 therethrough. Lumen 146 includes a proximal port 148 and defines an opening 150 for cutting tissue. Lumen 146 is couplable to a suction source 160 to provide suction through opening 150 to facilitate removal of tissue from a patient, as discussed in detail below. Tubular member 140 can be rotatably and/or longitudinally movable within lumen 126 of outer catheter 120. Preferably, outer catheter 120 and tubular member 140 are sealingly connected, such as by interposing one or more o-rings (not shown) between these two components of the medical device 110. Proximal end 142 of tubular member 140 can also be provided with a handle 147 for gripping by an operator such as a surgeon or other medical professional.

A variety of materials can be used to form tubular member 140. For example, tubular member 140 can be made of the same or similar material(s) as the outer catheter 120. It is also possible to configure tubular member 140 to have a desired constant or varying flexibility or stiffness along its length, as it is with outer catheter 120.

If made from plastic, outer catheter 120 and tubular member 140 can be manufactured from a single extrusion of material or from a multiple extrusion, such as a trilayer extrusion described in U.S. Pat. No. 6,165,166 to Samuelson et al. Other ways of making these components of the medical device 110 are possible. For example, outer catheter 120 and tubular member 140 can be formed by shrinking polymeric tubing in layers over a mandrel or by dipping a mandrel in molten plastic material to build up layers of plastic material. Layers of reinforcement material such as various metallic or fibrous braided material can be interposed between the layers of plastic material.

Figure 1B:
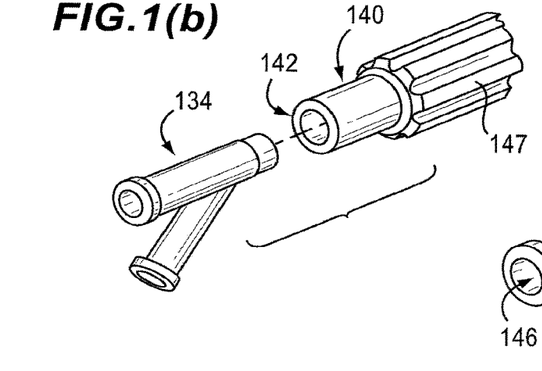
FIGS. 1(b)-1(d) are partial views of a portion of the medical device depicted in FIG. 1(a).
Figure 1C:
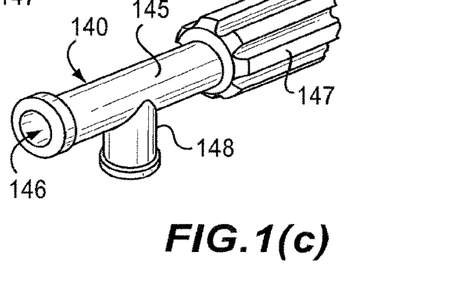

As discussed above, proximal port 148 is preferably in fluid communication with a suction source 160, described in detail below. Additionally or alternatively, a Luer connector 134 can be provided as depicted in FIG. 1(b), or proximal port 148 can be defined through sidewall 145 of member 140 as depicted in FIG. 1(c). The Luer connector 134 (FIG. 1(b)) can be used to couple the suction source 160 to the medical device 110, yet still permit introduction of other components and/or beneficial agents through lumen 146 during a surgical procedure. Saline solution is one example of what can be introduced through the lumen 146.

Figure 1D:
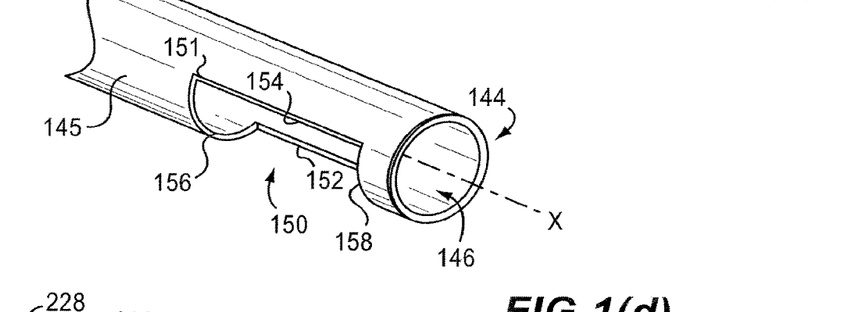

As depicted in FIG. 1(d), an opening 150 has an elongate shape and is defined in sidewall 145. The opening 150 is defined by two elongate substantially parallel edges 152 and 154.

One or both of the edges 152, 154 can be sharpened to serve as cutting members to facilitate removal of tissue from a patient. Additionally or alternatively, proximal and distal portions 156 and 158 of opening can be sharpened to form cutting members. Opening 150 can be defined by the same material(s) that form(s) the tubular member 140, or a separate insert can be disposed within the opening 150 to define its boundary and provide the cutting edge(s) of the opening 150. For example, if tubular member 140 is formed of a polymer, opening 150 can be defined by the same polymeric material, or can be formed from a metallic insert about which tubular member 140 is formed, such as by injection molding.

Regardless which portions 152, 154, 156, 158 of opening 150 are formed into cutting members, tissue that is cut from within the body of a patient can be removed from the patient's body by applying suction through opening 150 from suction source 160 such that the cut tissue is drawn through the medical device 110 and out of the patient's body. To cut or resect tissue within the patient's body, the distal end 144 of the tubular member (including at least a portion of the opening 150) is moved to place it distal of the distal end 124 of the outer catheter 120. Tissue can then be engaged within the opening 150 by manipulating the medical device 110, and the engaged tissue is then cut from the patient's body by moving the tubular member 140 in a longitudinal direction along longitudinal axis X and/or in a rotational direction about axis X with respect to the outer catheter 120. The cut or resected tissue is then removed from within the patient's body by the use of suction which draws it up through the lumen 146 and out of the patient's body.

While a sharpened edge of opening 150 has been described as acting as a cutting member for cutting tissue and thus allowing its removal from a patient's body, other mechanisms for cutting tissue within a patient's body are possible. For example, a cutting member can be provided in the form of an active cord cautery device such as a bipolar cautery device or a monopolar cautery device. Moreover, an ultrasound device 170 (see FIG. 1(a)) can be operably coupled to one or more edges 152, 154, 156, 158 of opening 150 to facilitate tissue removal.

A suction source can be operably coupled to the medical device to facilitate removal of tissue from a patient. As depicted in FIG. 1(a), suction source 160 can take the form of a constant vacuum that can be applied through the lumens 146 of the medical device 110. The suction source 160 can be provided at a wall connection in an operating room or other medical treatment area, or it can be a portable source of suction provided by a movable vacuum generator. The suction source 160 can be placed in fluid communication with the medical device 110 by way of a controllable valve 162 that can be opened or closed to apply a desired amount of suction through the medical device 110. The surgeon operating the medical device 110 or some other medical professional can operate the valve 162.

A collector 164 can be provided to collect tissue that is removed from a patient after it has been cut from the patient and suctioned out of the patient's body. The collector 164 could be a bag or some other type of container.

A light source can be provided to facilitate determination of the location of the opening of the medical device while inside a patient. For example, a light source 172 can be disposed on the medical device 110 to aid the operator of the device 110, as depicted in FIG. 1(a). The light source can include one or more fiber optic elements 174 and/or light emitting diodes 176. By using the light source 172, the positioning and/or location of the portion of the medical device 110 inserted into the body of the patient can be more easily and/or accurately determined, resulting in a more efficient surgical procedure.

Other elements can be included with a medical device as described herein to assist a surgeon or other medical professional in performing a surgical procedure using the medical device. For example, as depicted in FIG. 1(a), a computer interface 180 can be used to provide a visual image of the surgical site to the surgeon. As such, the computer interface can be operably coupled to one or more optical elements (such as elements 174) in visual communication with the surgical site.

In operation, a surgeon can introduce medical device 110 into a patient. Signals in the form of visual information are received through fiber optic elements 174 and directed to computer interface 180. Computer interface 180 is configured and adapted to display a representative image of the surgical site on a graphical user interface 182 as depicted in FIG. 1. Graphical user interface 182 can comprise a display panel configured to display a plurality of data objects 184, such as a window for displaying an image of the surgical site, touch screen menus and the like. A control panel 186 (such as a keyboard and pointing device, if desired) can also be provided to navigate through images collected of the surgical site.

Suitable fiber optic probes such as Spyglass™ fiber optic probes commercially available from Boston Scientific of Massachusetts can be used. Moreover, other types of imaging systems can be used in combination with the medical device of the present invention including, but not limited to, CT imaging, Magnetic Resonance Imaging, fluoroscopic and ultrasound imaging. Data obtained from each of these types of imaging systems can be routed through leads into computer interface 180 to provide a real time image of the surgical site. Moreover, it is possible and within the scope of the invention to use other computer assisted visual tools to perform a surgical procedure. For example, virtual imaging software can be used to simulate the surgical site based on data acquired through other means, such as position sensors.

A bag can be provided for collecting a tissue sample. For example, as depicted in FIG. 1(a), a bag 190 is provided for collecting a tissue sample. Bag 190 can be coupled to the distal end 144 of tubular member 140 of medical device 110 as depicted in FIG. 1(a), or can be introduced by means of a separate catheter (not shown). Bag 190 can be used to collect a sample in lieu of or in addition to suction from suction source 160.

Depicted in FIGS. 2(a)-5(d) are other embodiments of medical devices according to the invention. These devices also can be used to remove tissue from within the body of a patient, and these devices can be used with or without suction.

Figure 2A:
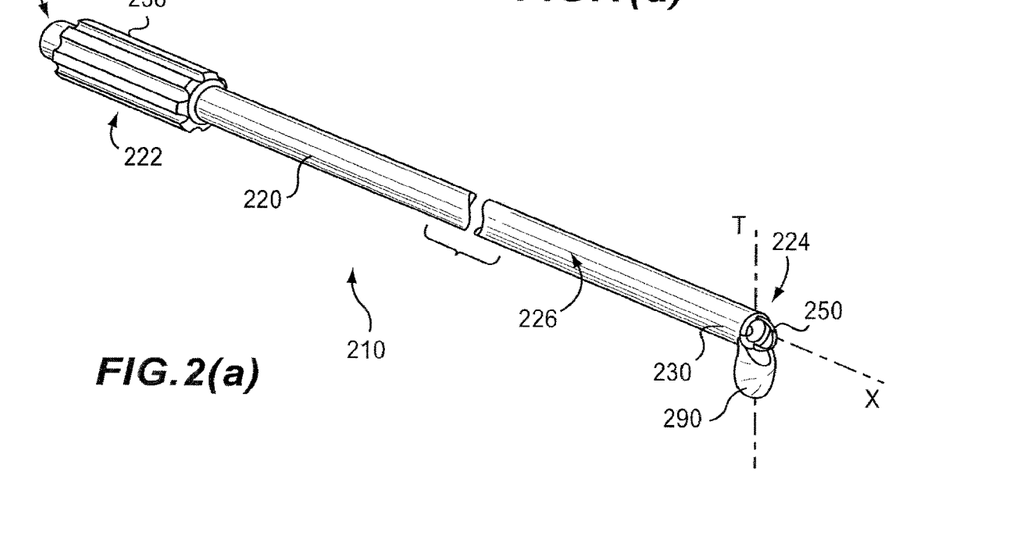
FIG. 2(a) is an isometric view of a second representative embodiment of a medical device made in accordance with the present invention.
Figures 2B, 2C, 2D:
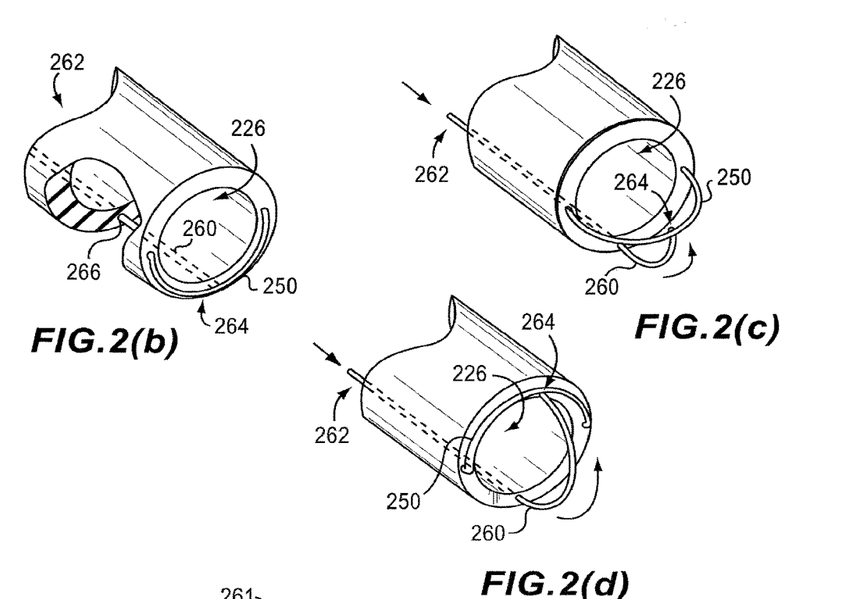
FIGS. 2(b)-2(d) are isometric views of a portion of the medical device depicted in FIG. 2(a).

As depicted in FIG. 2(a), a medical device 210 includes a main body portion 220, and the main body portion 220 includes a proximal end 222 and a distal end 224. Main body portion 220 extends along a longitudinal axis X. If desired, proximal end 222 of main body portion 220 can be affixed to and/or integrally formed with a handle portion 236. Main body portion 220 can be made from a variety materials as with portions 120, 140 of medical device 110. A cutting member 250 is operably coupled to the distal end 224 of the main body portion 220. As depicted in FIGS. 2(b)-2(d), cutting member 250 is configured to rotate and/or pivot about an axis T that is transverse to the longitudinal axis X from a first position as depicted in FIG. 2(b) to a second position as depicted in FIG. 2(d) when performing a cutting operation.

Medical device 210 can take on a variety of forms. While medical device 210 can be provided with a bag 290 for collecting tissue removed from a patient, main body portion 220 can define a lumen 226 along at least a portion of its length, the lumen having a distal port 230 at the distal end 224 of the medical device 210 and a proximal port 228 proximal to the distal end 224 of the medical device. The proximal port 228 can be in fluid communication with a suction source similar to the embodiment of FIG. 1(*a*) for removing tissue cut by the cutting member 250 through the lumen 226. The cutting member 250 can have an substantially arcuate shape and circumscribe a volume when moved from the first position to the second position that is substantially hemispherical.

Main body portion 220 can be made of a variety of materials and by a variety of methods as with outer catheter 120 described above. Also, main body portion 220 can have a uniform or increasing or decreasing stiffness along its length to provide the surgeon with the appropriate stiffness or flexibility required by the application at hand.

The cutting member 250 can be made from surgical grade steel. A variety of other materials could be used to form the cutting member. The cutting member 250 can be manufactured by stamping out an appropriately shaped piece of metal or by any of a variety of other processes.

As depicted in FIGS. 2(*b*)-2(*d*), an actuator 260 is provided. The actuator 260 can be a wire including a proximal end 262 and a distal end 264, with the distal end 264 of the actuator operably coupled to the cutting member 250. The distal end 264 of the actuator 260 can be configured to circumscribe an arcuate path when the proximal end of the wire 262 is moved along the longitudinal axis X, as shown in FIGS. 2(*b*)-2(*d*). Optionally, the wire can be received by a second lumen 266 traversing the length of the main body portion 220 of medical device 210. The actuator 260 can be made at least in part from spring steel with a distal end 264 that is biased to form an arc as disposed in FIG. 2(*d*). When actuator 260 is withdrawn into lumen 266 it straightens out until it is once again moved distally out of lumen 266. The cutting member 250 can be caused to move from the first position to the second position when the wire is advanced in a distal or proximal direction with respect to the main body portion. By way of further example, if desired, it is possible to form actuator 260 of a shape memory material such as an alloy of nickel and titanium (e.g., Nitinol™). Other materials can be used to form the actuator 260.

Figure 2E:
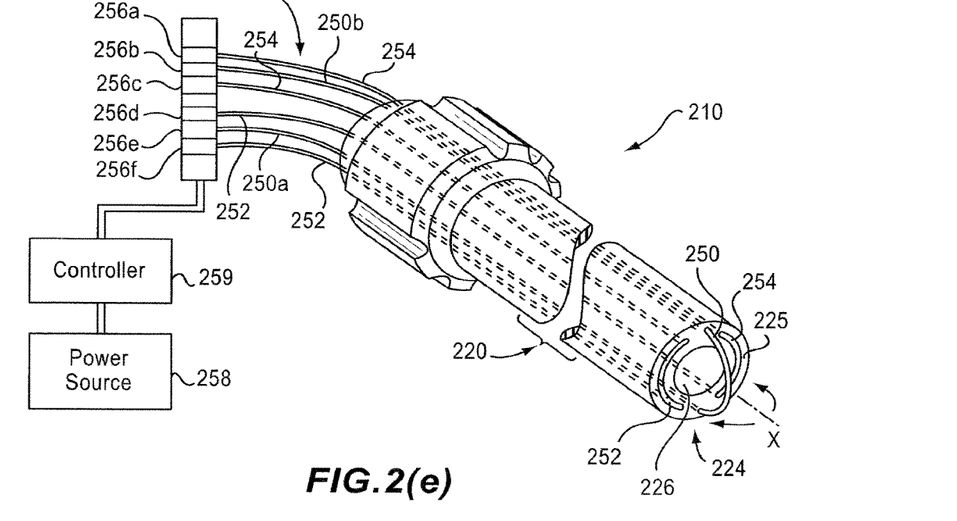
FIG. 2(e) is a schematic representation of an alternate embodiment of the medical device depicted in FIG. 2(a).

As depicted in FIG. 2(*e*), the medical device 210 includes the cutting member 250 and the cutting member 250 is moved between a first position and a second position by use of an electromagnetic force applied to the cutting member 250. In this embodiment, the actuator 260 and the cutting member 250 can be configured to carry electrical currents in opposing paths to create attractive and repulsive forces to cause a desired movement of the cutting member 250. For example, the cutting member 250 can be mounted on insulated electrical leads 250*a*, 250*b* that are routed to a switched power supply 258. Electrical loops 252 and 254 can be provided embedded in the face 225 of distal end 224 of main body portion 220 of medical device 210 that are also connected to the power supply 258. Electrical power can be routed through each of the circuits defined by loops 250*a*, 250*b*, 252 and 254, for example, by use of a switching mechanism having pin diodes 256(*a*)-(*f*) that are controlled by a controller 259. By sending electrical current through the cutting member 250 and loop 252 in opposite directions, a repulsive force can be achieved between the two conductors, causing cutting member 250 to pivot away from loop 252.

Similarly, by operating a current in the same direction through loop 254 and cutting member 250, an attractive force can be imposed between the two conductors. Thus, for example, by ramping and switching the direction of the current going through cutting member 250 and maintaining the directions of the current going through loops 252 and 254 in opposite directions, it is possible to cause cutting member 250 to oscillate between first and second positions. Other ways of actuating and moving the cutting member 250 are possible.

In operation, the medical device 210 of FIGS. 2(*a*)-2(*e*) can be used as follows. The medical device 210 is introduced into a patient and the cutting member 250 is positioned close to or in contact with tissue to be removed from within the body of the patient. For example, a medical device according to the invention can be inserted through a urethra of a patient to remove tissue from the patient's bladder or prostate. The actuator 260 can be actuated to move the cutting member 250 between the first position to the second position. As the cutting member 250 is moved from the first position to the second position, scalloped shaped pieces of tissue are removed from the patient. If a lumen of the medical device 210 is operably coupled to a suction source (such as the suction source 160 described above), substantially continuous removal of tissue can be accomplished through the lumen as the tissue is cut from within the patient's body by the cutting member 250.

Figures 3A, 3B, 3C, 3D:
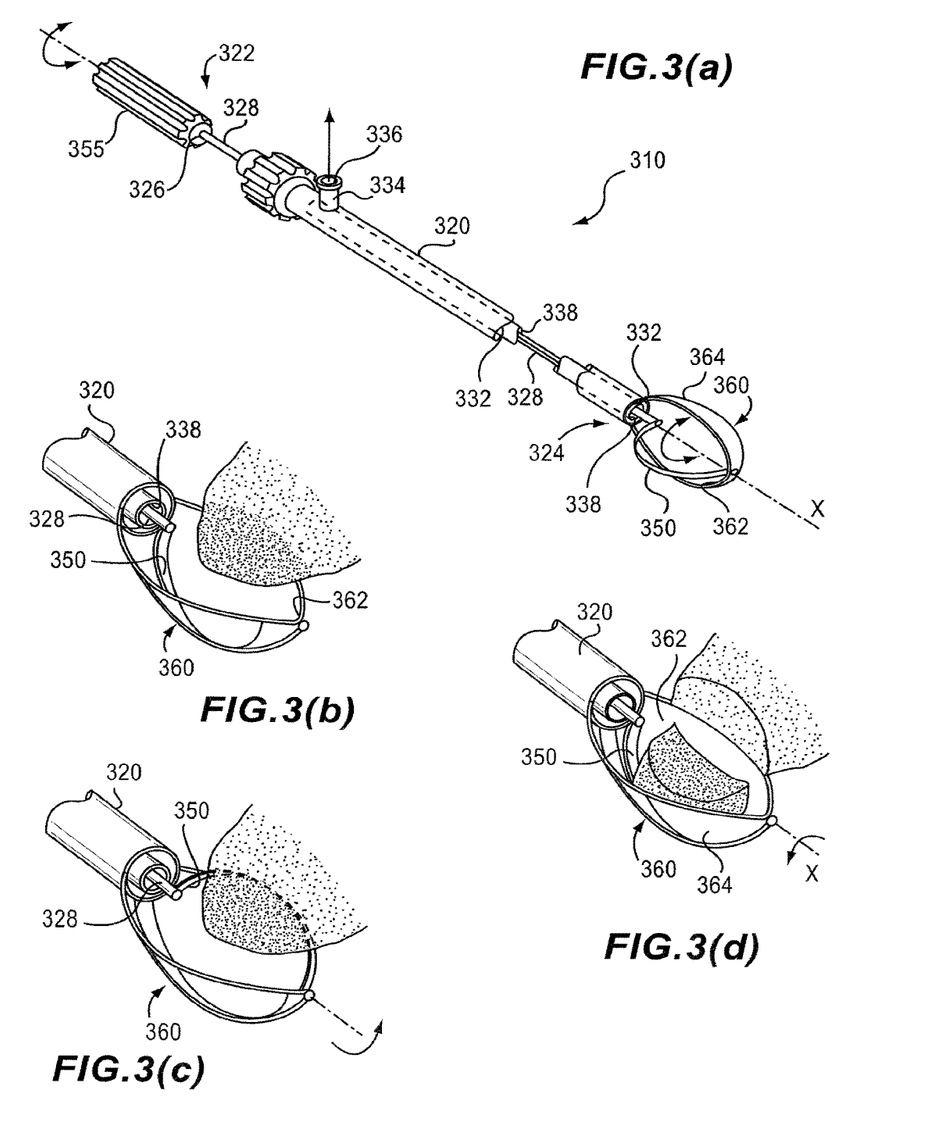
FIG. 3(a) is an isometric view of a third representative embodiment of a medical device made in accordance with the present invention.
FIGS. 3(b)-3(d) are isometric views of a portion of the medical device depicted in FIG. 3(a).

In accordance with another aspect of the invention, a medical device includes a main body portion, a shaft rotatably disposed in a lumen of the main body portion, and a substantially arcuate cutting member attached to the distal end of the shaft. As depicted in FIGS. 3(*a*)-3(*d*), a medical device 310 is provided including a main body portion 320 defining a lumen 326 through the main body portion 320, the main body portion 320 having a proximal end 322 and a distal end 324. A shaft 328 rotatable about a longitudinal axis X with respect to main body portion 320 is also provided, disposed in the lumen 326 of the main body portion 320. Additionally, a substantially arcuate cutting member 350 and compartment 360 are attached to the distal end 332 of the shaft. In one embodiment, cutting member 350 and compartment 360 are smaller than depicted in FIGS. 3(*a*)-3(*d*). Cutting member 350 and compartment 360 can be at least small enough to fit through the smallest cannula, incision or lumen that allows passage of the main body portion 320 of device 310. For illustrative purposes, cutting member 350 and compartment 360 are shown enlarged in FIGS. 3(*a*)-3(*d*) so that details of these elements can be seen more easily. In another embodiment, to permit resection of larger amounts of tissue, cutting member 350 and compartment 360 can be made larger or at least as shown in FIGS. 3(*a*)-3(*d*), in which case the main body portion 320 of device 310 can be introduced through a larger incision, lumen or cannula. Other shapes are possible instead of the substantially arcuate shape. The cutting member 350 is configured to circumscribe a volume about the longitudinal axis X when the shaft is rotated as depicted in FIGS. 3(*a*)-3(*d*).

A compartment 360 can be disposed at the distal end 324 of the main body portion 320 as depicted in FIG. 3(*a*)-3(*d*). Compartment 360 houses cutting member 350 when it is not in use, such as when medical device 310 is being introduced into or withdrawn from a patient. Compartment 360 can thus protect cutting member 350 from being damaged when not in use. Compartment 360 can also be used to capture pieces of tissue cut from a target area using cutting member 350. As depicted in FIGS. 3(a), 3(b) and 3(d), compartment 360 is defined by a solid hemispherical wall 364 having an interior surface 362.

Main body portion 320 and compartment 360 can be made of a variety of materials and by a variety of methods as with outer catheter 120 and main body portion 220 described above. Main body portion 320 can be attached to compartment 360 by various processes. For example, welding can be used to attached the main body portion 320 to the compartment 360. Alternatively, the main body portion 320 and the compartment 360 can be integrally formed together as one piece. The main body portion 320 can have a uniform or increasing or decreasing stiffness along its length.

The cutting member 350 can be made from a variety of materials as described above for cutting member 250. The cutting member 350 can also be manufactured in various ways, as with cutting member 250. The cutting member 350 can be formed from the same piece of material as shaft 328. If formed from the same piece of material, shaft 328 and cutting member 350 can be formed in tandem in a single manufacturing operation or in separate operations. Alternatively, cutting member 350 can be formed separately from shaft 328 and attached thereto, such as by welding or any other means known in the art. It is also possible to form both portions from the same piece of material. The cutting member 350 can be made from surgical grade steel, or another material can be used.

A rotational drive source 355 can be coupled to the proximal end 330 of the shaft 328. Drive source 355 can be a manual source, such as a handle for manual rotation as depicted in FIG. 3(a). Alternatively, drive source 355 can be a motor attached to shaft 328 by way of a rotational coupling.

By way of further example and as depicted in FIG. 3(a), cutting member 350 can be disposed within a compartment 360 affixed to the distal end 324 of the main body portion 320 as depicted in FIG. 3(a)-3(d). In operation, medical device 310 is introduced into a patient, and compartment 360 is placed proximate a target tissue area to be removed. Shaft 328 is then rotated with respect to main body portion 320, and cutting member 350 is rotated out of compartment 360, and about longitudinal axis X. As cutting member 350 is rotated outside of compartment 360, it slices through target tissue, separating the tissue from the patient. Once separated, the tissue is collected in compartment 360, at which point the tissue can be removed from the patent. To facilitate tissue removal, main body portion 320 can define a second lumen 334 therethrough. Second lumen 334 includes a distal port 338 proximate the cutting member 350 defined in the interior surface 362 of compartment 360 and a proximal port 336 proximal to the distal end 324 of the main body portion 320. To facilitate tissue removal, a suction source (such as suction source 160 described above) can be placed in fluid communication with proximal port 336 of lumen 334. Thus, as tissue is cut by cutting member 350 and collected by container 360, suction will draw morcellated tissue through distal port 338 and through second lumen 334.

Figures 4, 5A:
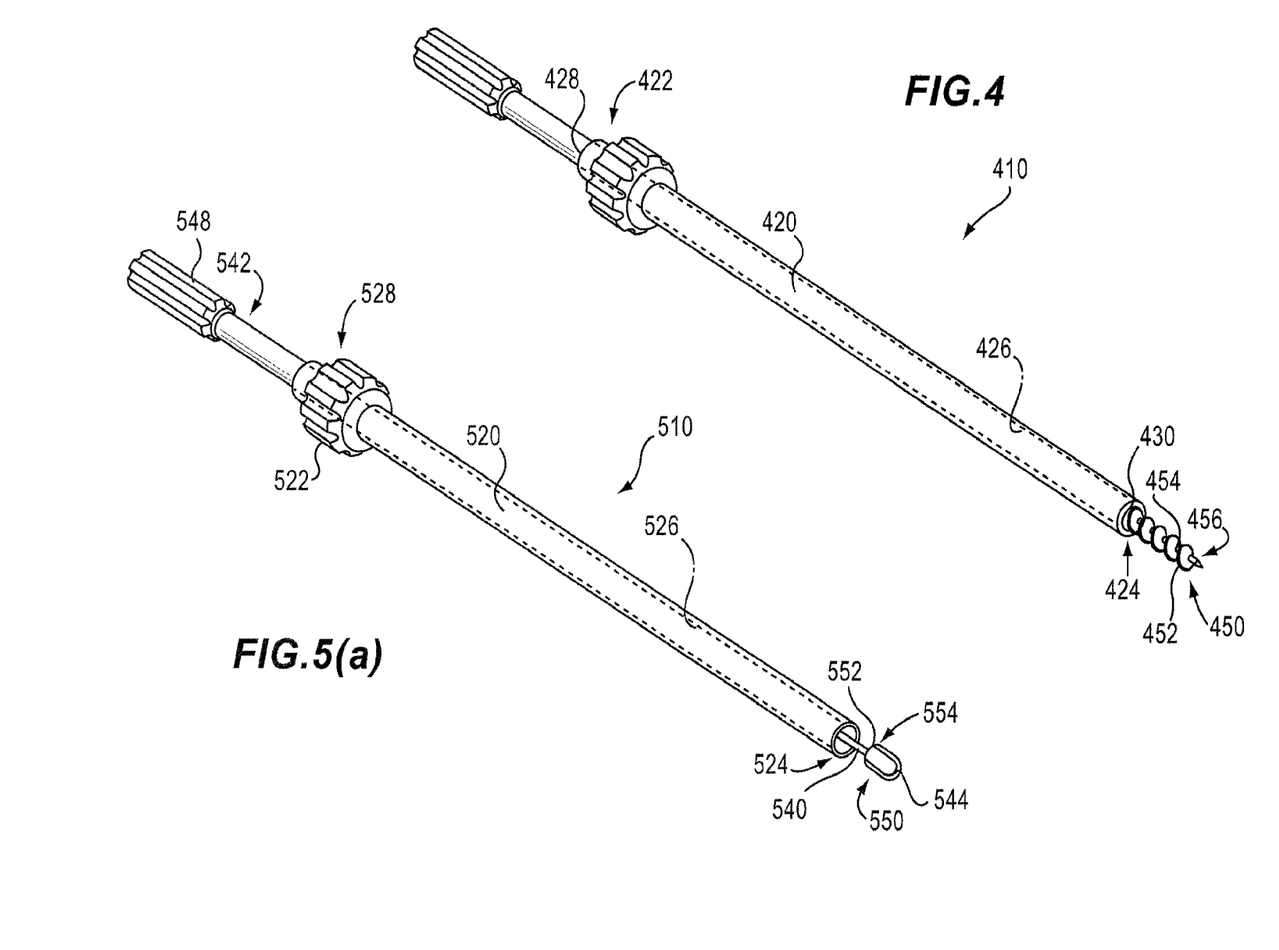
FIG. 4 is an isometric view of a fourth representative embodiment of a medical device made in accordance with the present invention.
FIG. 5(a) is an isometric view of a fifth representative embodiment of a medical device made in accordance with the present invention.

In accordance with still another aspect of the invention, a medical device includes a main body portion including a proximal end and a distal end, and the main body portion defines a lumen therethrough. The medical device further includes a rotatable cutting member disposed in the lumen. As depicted in FIG. 4, a medical device 410 includes a main body portion 420. The main body portion 420 includes a proximal end 422 and a distal end 424, and the main body portion 420 defines a lumen 426 therethrough with a proximal port 428 and a distal port 430. Medical device 410 further includes a cutting member 450 in the form of an auger that is disposed in the lumen 426. Cutting member 450 is rotatably and/or longitudinally movable within main body portion 420. Cutting member 450 includes at least one helical cutting edge 452 and defines at least one helical channel 454 therethrough that is in fluid communication with lumen 426. The auger 450 can be extended out of the lumen 426 and beyond the distal end 424 of the main body portion 420 through distal port 430, with or without suction being applied to proximal port 428 of lumen 426. It is possible to provide the auger 450 with varying configurations including different blade edge configurations and pitches.

Main body portion 420 can be made of a variety of materials and by a variety of methods as with outer catheter 320 described above. Likewise, main body portion 420 can have a varying or uniform stiffness along the length of catheter. The auger 450 can be made from any of a variety of materials such as surgical grade steel, and the auger 450 can be manufactured using any of a variety of processes such as forging, swaging, and machining.

In operation, the medical device 410 is introduced into a patient (such as through the urethra) and the auger 450 is positioned near or in contact with tissue to be removed from within the body of the patient (such as from the bladder or prostate gland). Distal end 456 of the auger 450 can be made to extend or protrude from distal end 424 of main body portion 420. Whether or not the auger 450 is extended out of the main body portion 420, rotational movement of the auger 450 with respect to main body portion 420 will grab tissue near or in contact with the auger 450. While rotating, the helical cutting edge 452 of the auger 450 slices tissue and carries it up the channel 454. If the lumen 426 is operably coupled to a suction source (such as the suction source 160 described above), substantially continuous removal of tissue can be accomplished through lumen as it is cut from the patient by the auger 450. Even without suction, the rotating auger 450 causes tissue to be drawn through the channel 454 and up into the lumen 426.

In accordance with another aspect of the invention, a medical device includes a main body portion with a shaft slidably disposed therein and a cup shaped cutting member attached to a distal end of the shaft. As depicted in FIGS. 5(a)-5(d), a medical device 510 includes a main body portion 520. The main body portion 520 includes a proximal end 522 and a distal end 524, and the main body portion 520 defines a lumen 526 therethrough. A handle 528 can be connected to the proximal end 522 of main body portion 520 for gripping by the surgeon or other operator of the medical device 510. Medical device 510 further includes a shaft 540 slidably disposed through the lumen 526 of the main body portion 520, and a cup shaped cutting member 550 attached to the distal end 544 of the shaft 540. Shaft 540 also can have a handle 548 attached to the proximal end 542 thereof for gripping. Cutting member 550 can have a cutting edge 552 disposed proximate to rim 554 of the cup shaped cutting member 550. The cutting member 550 is preferably configured to cut tissue when advanced in a proximal direction with respect to the main body portion 520 of the medical device 510.

Main body portion 520 can be made of a variety of materials and by a variety of methods as with main body portion 220 described above. Likewise, main body portion 520 can have a uniform or increasing or decreasing stiffness along the length thereof. The cutting member 550 can be made from a variety of materials, and the cutting member 550 can be manufactured using any of a variety of processes. Also, the cutting member 550 can be affixed to the shaft 540 in various ways such as welding.

In operation, medical device 510 can be configured as depicted in FIG. 5(a), wherein the cutting member 550 can protrude beyond the distal end 520 of the main body portion 520. In operation, main body portion 520 of medical device 510 can be held stationary within the patient by gripping handle 528, and, by gripping handle 548 shaft 540 carrying cutting member 550 can be advanced distally with respect to main body portion into or adjacent to a mass to be removed. Shaft 540 can then be withdrawn proximally causing cutting edge 552 to slice through and remove tissue and capture the removed tissue using cup shaped cutting member 550. Cutting member 550 can then be withdrawn into main body portion 520 of medical device 510 and flushed and cleaned by way or irrigation and suction through lumen 526 if sufficiently large or a second lumen, if needed, and then redeployed to collect more tissue, if desired.

Figure 5B:
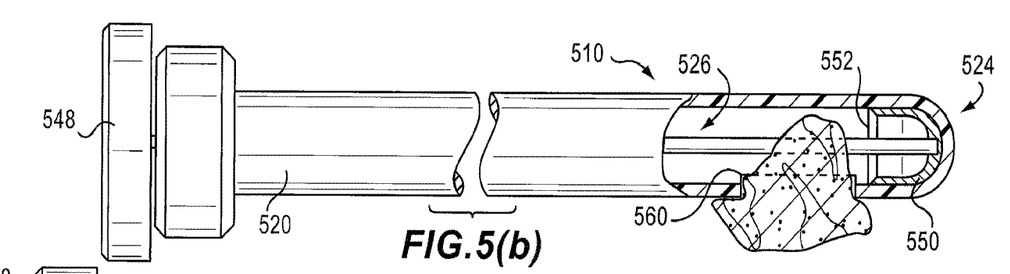
FIGS. 5(b)-5(d) are partial cross-sectional views of an alternate embodiment of the medical device depicted in FIG. 5(a).
Figure 5C:
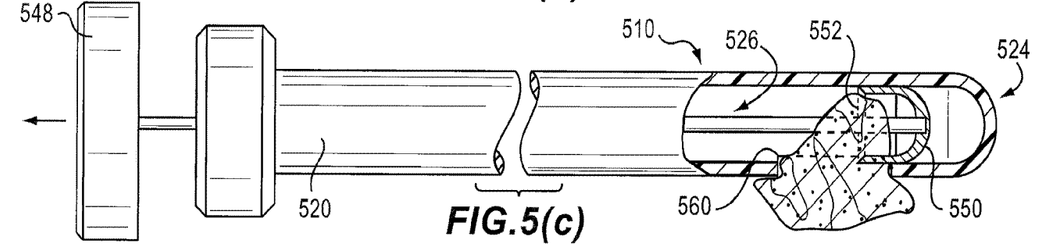
Figure 5D:
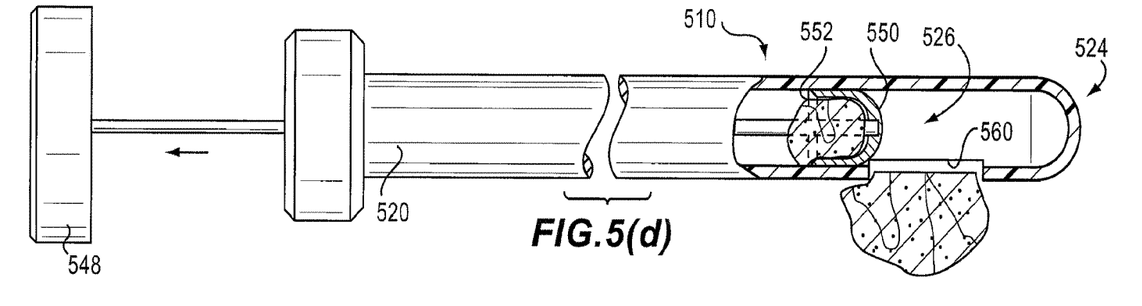

Alternatively, and as depicted in FIGS. 5(b)-5(d), main body portion 520 can be provided with a closed distal end 524 and define a tissue entry port 560 through a sidewall 525 of main body portion 520 suitable to permit entry of tissue to be removed from a patient. In accordance with this embodiment suction can be applied to lumen 526 to initiate a flow therethrough that draws tissue to be removed into port 560. Cutting member 550 can then be drawn proximally to cut the tissue from the patient, and the suction can cause the resected tissue to be removed through lumen 526.

In accordance with another aspect of the invention, a method of removing tissue from within the body of a patient includes the steps of providing a medical device (such as one of the medical devices described herein), introducing the medical device through the urethra of a patient, removing tissue from the patient by advancing a cutting member in a proximal direction with respect to the main body portion, and withdrawing the medical device from the patient. The method can be used to remove tissue from the bladder and/or prostate gland of the patient, for example.

Particular embodiments according to the invention are described and shown herein, but the invention is not limited to these particular embodiments. Various modifications, additions, and deletions can be made to the embodiments described and shown herein without departing from the spirit or scope of the invention. Also, the various features described and/or shown with respect to the embodiments can be combined in various ways even if not specifically described or shown in those combinations.

What is claimed is:

1. A medical device, comprising:
a handle;
an assembly extending along a longitudinal axis between a proximal end and a distal end, the proximal end of the assembly being coupled to the handle and the distal end of the assembly including an opening, the opening defining a passageway extending transverse to the longitudinal axis and communicating between a lumen defined by the assembly and an exterior of the assembly;
a rotating drive shaft extending within the lumen of the assembly; and
a rotating cutting member, wherein a proximalmost end of the rotating cutting member is coupled to the rotating drive shaft, wherein the proximalmost end of the rotating cutting member is positioned closer to the opening than the handle, and wherein the proximalmost end of the rotating cutting member extends distally of a distal end of the rotating drive shaft;
wherein in a first configuration, the rotating cutting member has a first orientation relative to the opening, and in a second configuration, the rotating cutting member has a second orientation relative to the opening, the second orientation being rotated about the longitudinal axis of the assembly relative to the first orientation.

2. The device of claim 1, wherein the rotating cutting member includes a cutting edge to facilitate cutting of tissue.

3. The device of claim 1, wherein a proximal end of the rotating drive shaft is coupled to an actuator of the handle.

4. The device of claim 1, wherein the assembly is fixed longitudinally and rotationally to the handle.

5. The device of claim 1, further including:
a port in communication with the lumen of the assembly.

6. The device of claim 5, wherein the port is coupled to an aspiration source.

7. The device of claim 1, wherein the assembly includes a cylindrical shaft.

8. The device of claim 1, wherein movement of the rotating cutting member between the first orientation and the second orientation is configured to sever tissue.

9. The device of claim 8, wherein the tissue is bladder or prostate tissue.

10. The device of claim 1, wherein the rotating cutting member includes a single straight blade member.

11. A medical device, comprising:
a handle having an actuator;
an assembly extending along a longitudinal axis between a proximal end and a distal end, the proximal end of the assembly being coupled to the handle and the distal end of the assembly including an opening, the opening extending radially through a side wall of the assembly and defining a passageway extending transverse to the longitudinal axis and communicating between a lumen defined by the assembly and an exterior of the assembly;
a rotating drive shaft extending within the lumen of the assembly and operably coupled to the actuator; and
a rotating cutting member including an arcuate-shaped cutting member, a proximalmost end of the rotating cutting member being coupled to the rotating drive shaft, wherein the proximalmost end of the rotating cutting member is positioned closer to the opening than the handle, and wherein the proximalmost end of the rotating cutting member extends distally of a distal end of the rotating drive shaft;
wherein in a first configuration, the rotating cutting member has a first orientation relative to the opening, and in a second configuration, the rotating cutting member has a second orientation relative to the opening, the second orientation being rotated about the longitudinal axis of the assembly relative to the first orientation.

12. The device of claim 11, further including:
a port in communication with the lumen of the assembly.

13. The device of claim 12, wherein the port is coupled to an aspiration source.

14. The device of claim 11, wherein the assembly is fixed longitudinally and rotationally to the handle.

15. The device of claim 11, wherein the rotating cutting member includes a cutting edge to facilitate cutting of tissue, wherein the tissue is bladder or prostate tissue.

16. A medical device, comprising:
an assembly extending along a longitudinal axis between a proximal end and a distal end, the distal end of the assembly including an opening, the opening extending radially through a side wall of the assembly and defining a passageway extending transverse to the longitudinal axis and communicating between a lumen defined by the assembly and an exterior of the assembly;

a rotatable drive shaft extending within the lumen of the assembly; and a cutting member, a proximalmost end of the cutting member being positioned at the distal end of the assembly and the proximalmost end of the rotating cutting member extending distally of a distal end of the rotatable drive shaft and wherein the proximalmost end of the cutting member is positioned closer to the opening than a handle.

17. The device of claim 16, wherein in a first configuration, the cutting member has a first orientation relative to the opening, and in a second configuration, the cutting member has a second orientation relative to the opening, the second orientation being rotated about the longitudinal axis of the assembly relative to the first orientation.

18. The device of claim 16, wherein the cutting member includes a cutting edge to facilitate cutting of tissue, wherein the tissue is bladder or prostate tissue.

19. The device of claim 16, wherein the cutting member is arcuate and includes a radially outer surface and a radially inner surface, wherein a longitudinal edge of the cutting member is configured to sever tissue such that tissue is urged by the radially inner surface into the lumen.

* * * * *